United States Patent [19]
Hallberg et al.

[11] Patent Number: 5,350,767
[45] Date of Patent: Sep. 27, 1994

[54] DERIVATIVES OF CYSTEINE

[75] Inventors: Anders R. Hallberg, Lund; Per A. S. Tunek, Malmö both of Sweden

[73] Assignee: Aktiebolaget Draco, Lund, Sweden

[21] Appl. No.: 936,615

[22] Filed: Aug. 27, 1992

Related U.S. Application Data

[60] Division of Ser. No. 626,391, Dec. 12, 1990, abandoned, which is a continuation of Ser. No. 272,138, Nov. 16, 1988, abandoned.

[30] Foreign Application Priority Data

Nov. 19, 1987 [SE] Sweden .................. 8704542

[51] Int. Cl.$^5$ ................................. A61K 31/195
[52] U.S. Cl. .................................... 514/562
[58] Field of Search ......................... 514/562

[56] References Cited

FOREIGN PATENT DOCUMENTS 1208452  1/1966  Fed. Rep. of Germany .
954268   4/1964  United Kingdom .

Primary Examiner—Michael L. Shippen
Attorney, Agent, or Firm—White & Case

[57] ABSTRACT

A compound of the formula

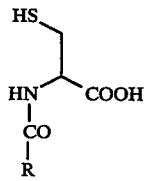

wherein R is —CH(CH$_3$)$_2$ or —C(CH$_3$)$_3$ or a physiologically acceptable salt or optical isomer thereof useful for the treatment of particularly different lung diseases.

3 Claims, No Drawings

DERIVATIVES OF CYSTEINE

This application is a divisional of application Ser. No. 07/626,391, filed on Dec. 12, 1990 (abandoned), which is a continuation of application Ser. No. 07/272,138 filed Nov. 16, 1988 (abandoned).

TECHNICAL FIELD

The present invention relates to new derivatives of cysteine with anti-inflammatory effect, a process for their preparation, pharmaceutical compositions containing them and a method of their pharmacological use.

The object of the invention is to provide an anti-inflammatory cysteine derivative. Such a substance will be useful in the treatment of different diseases.

PRIOR ART

N-acetyl-L-cysteine has been used as a therapeutic agent against e.g. chronic bronchitis for over 20 years. A patent with the title "Decongestant Compositions comprising N-acetylated Sulphydryl Compounds" (GB 954268) was published in 1964.

Following the early investigations and patents, N-acetyl-L-cysteine has been used extensively, primarily against obstructive lung disease like chronic bronchitis claimed to act as a mucolytic. In addition, this compound has been used as an antidote against liver toxicity caused by paracetamol overdose.

N-butyrylcysteine is disclosed in DE 1208450 as an ingredient for a hair preparation.

DISCLOSURE OF THE INVENTION

According to the present invention it has been found that a compound of the formula

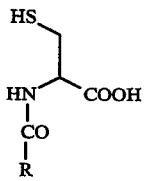

I wherein R is —CH(CH$_3$)$_2$ or —C(CH$_3$)$_3$ or a physiologically acceptable salt thereof or optical isomer thereof has a much better bioavailability following oral intake than has N-acetyl-L-cysteine. Thus, after oral intake the new compounds will reach levels in the systemic circulation that are orders of magnitude higher than are maximal levels of N-acetyl-L-cysteine. Since the compounds of formula I have similar or identical potentials as N-acetyl-L-cysteine to 1) break disulfide bridges, 2) act as anti-oxidants and 3) act as radical scavengers, oral treatment with the new substances should be much more effective than N-acetyl-L-cysteine against lung disease, provided that the disease is caused or maintained by some sort of oxidative stress.

It must also be pointed out, that another consequence of the biological stability of the compounds of formula I is that very little, if any, L-cysteine will be liberated. This means that these compounds will give rise to only very low levels of glutathione precursors. Therefore, the effects in the oxygen toxicity system described below are likely to be dependent on the synthetic thiols themselves, and not on glutathione biosynthesis.

The invention thus provides compounds, and physiologically acceptable salts and isomers thereof, which are useful in the therapeutic treatment of inflammatory lung diseases, such as chronic bronchitis, and other diseases, such as 1) other lung diseases complicated by viscous mucus like cystic fibrosis, asthma and emphysema,
2) connective tissue diseases like rheumatoid arthritis,
3) lung injury diseases like septic shock, ARDS and bronchopulmonary dysplasia,
4) diseases caused by radiation like gamma ray induced pneumonitis and fibrosis,
5) diseases in the lung parenchyma like sarcoidoses, fibrosis, granulomatosis, collagenosis, and
6) diseases associated with diabetes like destruction of B-cells and retinopathy.

Within the scope of this invention are also included physiologically acceptable salts of the compounds of the formula I, such as the salts of sodium, ammonium, calcium or magnesium, together with the non-toxic acid addition salts thereof.

The compounds of the formula I exist in two different optical forms, L and D isomers:

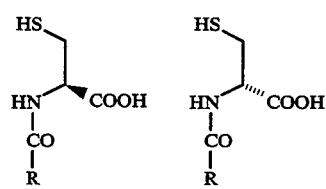

which both are included in this invention.

Pharmaceutical Preparations

According to the present invention the compounds of the formula I will be administered orally, in the form of pharmaceutical preparations comprising the active ingredient either as a free base or as a pharmaceutically acceptable non-toxic, acid addition salt, in association with a pharmaceutically acceptable carrier. The carrier may be a solid, semisolid or liquid diluent or capsule. Usually the active substance will constitute between 0.2 and 50% by weight for preparations suitable for oral administration.

To produce pharmaceutical preparations containing a compound of the formula I in the form of dosage units for oral application the selected compound may be mixed with a solid pulverulent carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol waxes, and the like, and then compressed to form tablets. If coated tablets are required, the cores, prepared as described above, may De coated with a concentrated sugar solution which may contain, e.g. gum arabic, gelatine, talcum, titanium dioxide, and the like. Alternatively, the tablet can be coated with a laquer dissolved in a readily volatile organic solvent or mixture of organic solvents. Dyestuffs may be added to these coatings in order to readily distinguish between tablets containing different active substances or different amounts of the active compounds.

For the preparation of soft gelatine capsules (pearl-shaped closed capsules) consisting of gelatine and for example, glycerol or similar closed capsules, the active substance may be admixed with a vegetable oil. Hard gelatine capsules may contain granules of the active substance in combination with solid, pulverulent carriers such as lactose, saccharose, sorbitol, mannitol, starches (e.g. potato starch, corn starch or amylopectin), cellulose derivatives or gelatine.

Liquid preparations for oral application may be in the form of syrups or suspensions, for example, solutions containing from about 0.2% to about 0% by weight of the active substance herein described, the balance being sugar and mixture of ethanol, water, glycerol, and propylene glycol. Optionally such liquid preparations may contain colouring agents, flavouring agents, saccharine and carboxymethyl-cellulose as a thickening agent.

Suitable daily doses of the compounds of the invention in therapeutical treatment of humans are 100 to 1.200 mg at peroral administration.

Methods of Preparation

The compounds of the invention may be obtained by any of the following methods:

A. The compound of the formula

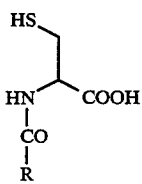

wherein R is —CH(CH₃)₂ or —C(CH₃)₃ or an optical isomer thereof, can be obtained by reaction of a compound of the formula

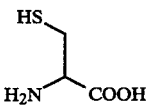

or an optical isomer thereof with an acylating agent of the formula

RCOX wherein R has the meaning given above and —COX is a reactive group capable of reacting with an amino group under formation of an amide moiety.

The acylating agent can for instance be an anhydride

or alternatively an acid halide, an amide, an activated acid or ester, tiolacid, silicic esters, acyloxyborane, methylselenolester, thiolester, acylazide, α-ketonitrile or a trihalo ketone.

B. The compound of the formula

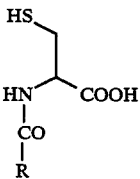

wherein R is —CH(CH₃)₂ or —C(CH₃)₃ or an optical isomer thereof, can be obtained by reducing a compound of the formula

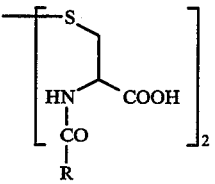

wherein R has the meaning given above or an optical isomer thereof, with a reducing agent, or electrochemically.

The reducing agent can be a metal, for instance zinc in dilute hydrogen chloride.

C. The compound of the formula

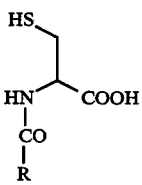

wherein R is —CH(CH₃)₂ or —C(CH₃)₃ or an optical isomer thereof, can be obtained by splitting off the protective group R¹ of a compound of the formula

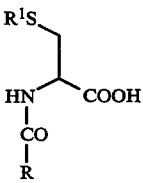

or an optical isomer thereof, wherein R has the meaning given above and R¹ is a protective group by the use of a reducing agent or by acidolysis.

The reducing agent can for instance be sodium or hydrogen/palladium.

The acidolysis can be performed by the use of for instance trifluoroacetic acid or hydrogen chloride in chloroform.

The protective group R¹ is for instance a benzyl, diphenylmethyl or triphenylmethyl group.

The compounds with the protected sulphur atom which are starting material in processes A and C above are obtained via protection of the S-atom of cysteine (racemic or optical isomer) followed by N-acylation of the S-protected cysteine.

D. The compound of the formula

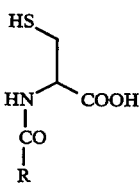

wherein R is —CH(CH₃)₂ or —C(CH₃)₃ or an optical isomer thereof, can be obtained by hydrolysis of a compound of the formula

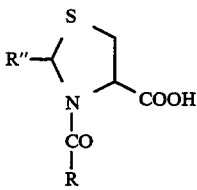

or an optical isomer thereof, wherein R has the meaning given above and R" is a protective group.

The protective group R" is for instance aryl, benzyl, hydrogen, a straight or branched alkyl chain consisting of 1-5 carbon atoms, such as methyl, ethyl, propyl, butyl.

The compound of the formula

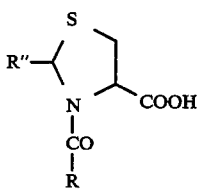

is obtained from reactions of cysteine or optical isomers thereof with the proper aldehyde to provide the corresponding thiazolidine which is acylated by the methods described in process A.

WORKING EXAMPLES

Example 1

Preparation of N-isobutyryl-L-cysteine

A suspension of 35.2 g (0.20 mol of L-cysteine hydrochloride monohydrate in 100 ml of a mixture of 80% of tetrahydrofuran (THF) and 20% of water was stirred under nitrogen at room temperature and treated with 44.0 g (0.40 mol of sodium isobutyrate. The reaction mixture (white slurry) was cooled to 0°–5° C. and, under nitrogen, 35 ml (0.21 mol) of isobutyryl anhydride was added dropwise. The resulting mobile suspension was stirred for 6 h at room temperature, allowed to stand overnight, and finally heated under reflux for 4 h. The reaction mixture was cooled on an ice bath and 18 ml of concentrated hydrogen chloride was added. The organic phase was evaporated to give a colourless oil. The oil was washed with hexane and thereafter treated with ether to give 12.9 g of the title compound as a white solid, mp 103°–104° C. (recrystallized from butyl acetate), $[\alpha]_D^{25} = +23.4°$ C. (c 5.0, $H_2O$, pH=7.0), $^1$H-NMR (CDCl₃): δ1.2 (6H, d, CH₃), 1.4 (1H, t, SH), 2.5 (1H, sept, CH), 3.1 (2H, m, CH₂), 4.9 (1H, dt, NCH), 6.7 (1H, d, NH), 10.6 (1H, s, OH). $^{13}$C-NMR (CDCl₃): δ19, 19.5; 26.5; 36; 54, 172, 178. ms: 335 (M⁺+2TMS, after silylation).

Example 2

Preparation of N-isobutyryl-D-cysteine

The compound was prepared according to the procedure described in example 1 (starting from the D-cysteine salt) and exhibited identical physical data. $[\alpha]_D^{25} = -23.4°$ (c 5.0, $H_2O$).

Example 3

Preparation of N-pivaloyl-L-cysteine

To a solution of 17.6 g (0.10 mol) of L-cysteine hydrochloride monohydrate in 50 ml of a mixture of 80% of tetrahydrofuran (THF) and 20% of water, under nitrogen, 24.8 g (0.20 mol) of sodium pivaloylate was added under stirring. The thick slurry was cooled on an ice bath and 21.3 ml (0.105 mol) of pivaloyl anhydride was added dropwise under 15 minutes. After addition of 50 ml of a mixture of 80% of THF and 20% of water, the reaction mixture was stirred for 2 hours in room temperature and was thereafter refluxed for 0.5 h. After cooling on an ice bath, 8.5 ml of concentrated hydrogen chloride was added. The organic phase was evaporated and the crude product was washed several times with hexane and thereafter dissolved in 150 ml chloroform. After filtration and evaporation of the solvent, the crude product was recrystallized from ethylacetate to give 8.2 g of the title compound as a white solid, mp 140° C., $[\alpha]_D^{25} = +39.0°$ C. (c=5.0, $H_2O$, pH=7.0). $^1$H-NMR (CDCl₃): δ1.2 (9H, s, CH₃), 1.4 (1H, t, SH), 3.1 (2H, m, CH₂), 4.9 (1H, dt, NCH), 6.7 (1H, d, NH), 10.6 (1H, s, OH). $^{13}$C-NMR (CDCl₃): δ26, 27, 39, 53, 163, 180. ms: 349 (M⁺+2TMS, after silylation).

Example 4

Preparation of N-pivaloyl-D-cysteine

The compound was prepared according to the procedure described in example 3 (starting from the D-cysteine salt) and exhibited identical physical data. $[\alpha]_D^{25} = -39.0°$ (c=5.0, $H_2O$, pH=7.0).

Example 5

Preparation of N-isobutyryl-D,L-cysteine

The compound was prepared according to the procedure described in example 1 (starting from the (racemic) D,L-cysteine salt) and exhibited identical physical data. $[\alpha]_D^{25} = 0°$ (c=5.0, $H_2O$).

Example 6

Preparation of N-pivaloyl-D,L cysteine

The compound was prepared according to the procedure described in example 3 (starting from the (racemic) D,L cysteine salt) and exhibited identical physical data. $[\alpha]_D^{25} = 0°$ (c=5.0, $H_2O$, pH=7.0).

Example 7

For the preparation of tablets the following compositions were made.

| Formulation A | |
| --- | --- |
| Active ingredient | 50 g |
| Lactose | 85 g |
| Potatoe starch | 40 g |
| Polyvinylpyrrolidone | 5 g |
| Cellulose Avicel | 18 g |
| Magnesium stearate | 2 g |
| Formulation B | |

-continued

| | |
|---|---|
| Active ingredient | 100 g |
| Lactose | 90 g |
| Potatoe starch | 50 g |
| Polyvinylpyrrolidone | 5 g |
| Cellulose Avicel | 23 g |
| Magnesium stearate | 2 g |

From the above compositions of Formulations A and B 1000 tablets were made, containing 50 mg and 100 mg of active substance, respectively. If desired, the obtained tablets can be film coated with e.g. methyl cellulose in an organic solvent.

| Formulation C 1 ml contains: | |
|---|---|
| Active ingredient | 30.0 mg |
| Sorbitol | 150.0 mg |
| Glycerol | 100.0 mg |
| Disodium Edetate | 0.5 mg |
| Metagin | 0.6 mg |
| Propagin | 0.3 mg |
| Essence Orange | 0.05 mg |
| Essence Lemon | 0.05 mg |
| Aethanol | 20.0 mg |
| Sodium Hydroxide | 10.0 mg |
| Purified Water | to 1.0 ml |

Metabolic Experiments

One object of the present invention is to provide molecules which after oral intake would give high levels of free thiols in plasma and ultimately in the lung. Therefore, experiments were performed to investigate biological stability and bioavailability of the compounds of formula I, and to compare these with N-acetyl-L-cysteine.

In vitro animal data

N-Acetyl-L-cysteine was rapidly hydrolyzed to yield L-cysteine in homogenates of liver, intestinal mucosa, and lung from rat. N-Isobutyryl-L-cysteine and N-pivaloyl-L-cysteine were not hydrolyzed to any measureable extent in vitro.

The hydrolysis of N-acetyl-L-cysteine took place predominantly in the cytosolic cell compartment.

To summarize, the hydrophilic N-acetyl derivative of L-cysteine was hydrolyzed in the soluble cell fraction, presumably by acyl-CoA transferases. The branched derivatives, N-isobutyryl- and N-pivaloyl-L-cysteine were not hydrolyzed in any cell compartment.

In vivo animal data

The thiols were injected into the intestines of anaesthetized rats. At various times after the injections blood samples were withdrawn, and plasma thiols analysed. The concentrations of the thiols in plasma were: N-isobutyryl-L-cysteine 13.0+2.9 $\mu$M (n=9), N-pivaloyl-L-cysteine 11.8+2.9 $\mu$M (n=9), and N-acetyl-L-cysteine 0.7 $\mu$M (only one experiment performed). The values given represent mean ±SEM, unless otherwise stated.

The results show that the plasma thiol levels obtained in vivo are related to the biological stability determined in vitro. Thus, a readily hydrolyzable compound like N-acetyl-L-cysteine was barely detectable in plasma after intraintestinal injection, while N-isobutyryl-L-cysteine, which was not hydrolyzed in vitro, reached considerable concentrations.

Data obtained in human volunteers

Plasma concentrations and urinary excretion in healthy human volunteers were measured after oral intake of N-acetyl-L-cysteine, and N-isobutyryl-L-cysteine, 1.23 mmole of each. The peak plasma concentrations of the free thiols were <1 $\mu$M, and 10 $\mu$M, respectively. The percentages of the doses excreted unchanged in urine were 2%, and 74%.

Summary of metabolic experiments

The experiments described above have shown that N-acetyl-L-cysteine is biologically unstable, and that this leads to a poor bioavailability after oral intake. Modification of the acyl moiety dramatically improved the biological stability and also the bioavailability. Thus, N-isobutyryl-L-cysteine reached high concentrations in plasma, and presumably also will reach the lung to a much higher extent than N-acetyl-L-cysteine.

Effect Measurements

Exposure to pure oxygen leads to lung oedema. The mechanism is that the increased oxygen pressure leads to incomplete reduction of oxygen and consequently to formation of activated oxygen species like superoxide, peroxides and hydroxyl radicals. Some of these activated oxygen species are identical to those formed during inflammation.

Other researchers have shown that N-acetyl-L-cysteine infused intravenously protects partially against oxygen-induced oedema in rats. We have confirmed these findings and have also demonstrated that N-isobutyryl-L-cysteine affords protection that is slightly better, when administered in the same way. The indicated above, the concentration of N-isobutyryl-L-cysteine in human plasma after oral intake, peaked at 10 $\mu$M. Therefore, it seems fully possible to obtain protection against oxidative stress and maybe against inflammation in lung by oral intake of our new thiols.

Conclusions

Metabolic studies demonstrated that N-isobutyryl-L-cysteine and N-pivaloyl-L-cysteine were much more biologically stable than the therapeutically used N-acetyl-L-cysteine. The plasma levels of the compounds after oral intake were much higher than levels of N-acetyl-L-cystein. The oxygen toxicity model indicated that the new compounds protected against lung injury at least as effectively as N-acetyl-L-cysteine after intravenous administration. The results indicate that the new compounds will be much more effective than N-acetyl-L-cysteine against oxidative stress in lung when given orally.

We claim:

1. A method for the treatment of lung diseases in mammals caused or maintained by oxidative stress, which comprises oral administration to a subject in need of such treatment of an effective amount of a pharmaceutical composition comprising as the active ingredient an effective amount of a compound of the formula:

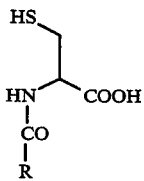 (I)

wherein R is —CH(CH₃)₂ or —C(CH₃)₃ or a physiologically acceptable salt or an optical isomer thereof.
2. A method according to claim 1, wherein R is —CH(CH₃)₂.
3. A method according to claim 1, wherein the optical isomer is the D-isomer.

* * * * *

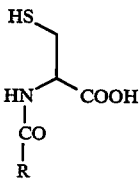 (I)

wherein R is —CH(CH₃)₂ or —C(CH₃)₃ or a physiologically acceptable salt or an optical isomer thereof.
2. A method according to claim 1, wherein R is —CH(CH₃)₂.
3. A method according to claim 1, wherein the optical isomer is the D-isomer.

* * * * *